United States Patent
Li (10) Patent No.: US 9,679,376 B2
(45) Date of Patent: Jun. 13, 2017

(54) MEDICAL IMAGE PROCESSING APPARATUS, METHOD, AND RECORDING MEDIUM

(71) Applicant: FUJIFILM Corporation, Tokyo (JP)

(72) Inventor: Yuanzhong Li, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/842,169

(22) Filed: Sep. 1, 2015

(65) Prior Publication Data

US 2016/0086327 A1 Mar. 24, 2016

(30) Foreign Application Priority Data

Sep. 22, 2014 (JP) ................. 2014-192152

(51) Int. Cl.
*G06K 9/00* (2006.01)
*G06T 7/00* (2017.01)
*G06K 9/62* (2006.01)
*G06T 11/60* (2006.01)
*H04N 13/02* (2006.01)
(Continued)

(52) U.S. Cl.
CPC .......... *G06T 7/0012* (2013.01); *A61B 5/0073* (2013.01); *G06K 9/6267* (2013.01); *G06T 11/60* (2013.01); *H04N 13/02* (2013.01); *G06T 2207/10072* (2013.01); *G06T 2207/10116* (2013.01); *G06T 2207/30008* (2013.01); *G06T 2207/30012* (2013.01); *G06T 2210/41* (2013.01); *H04N 2013/0092* (2013.01)

(58) Field of Classification Search
USPC ....... 382/100, 103, 107, 128–133, 162, 168, 382/173, 181, 203, 232, 254, 274, 276, 382/287–294, 305, 312, 316, 219; 600/407, 425, 476; 378/4, 21
See application file for complete search history.

(56) References Cited

U.S. PATENT DOCUMENTS

| 8,014,575 B2 * | 9/2011 | Weiss .................. B60R 25/00 382/128 |
| 2009/0234217 A1 * | 9/2009 | Mire .................. G06F 19/3437 600/407 |

(Continued)

FOREIGN PATENT DOCUMENTS

| JP | 2009-240617 A | 10/2009 |
| JP | 2009-254600 A | 11/2009 |
| JP | 2011-131040 A | 7/2011 |

OTHER PUBLICATIONS

Meelis Lootus et al., "Vertebrae Detection and Labelling in Lumbar MR Images," MICCAI Workshop: Computational Methods and Clinical Applications for Spine Imaging, 2013.
(Continued)

*Primary Examiner* — Seyed Azarian
(74) *Attorney, Agent, or Firm* — Sughrue Mion, PLLC (57) ABSTRACT

A determination unit makes a determination as to whether or not at least either one of at least a portion of an upper end vertebra and at least a portion of a lower end vertebra is included in a first medical image of a subject. If the determination is negative, an image obtaining unit obtains a second medical image that allows recognition of a label of the vertebra of the subject. A labeling unit aligns the first medical image with the second medical image and labels the vertebra included in the first medical image.

11 Claims, 5 Drawing Sheets

(51) Int. Cl.
*A61B 5/00* (2006.01)
*A61B 5/05* (2006.01)
*H04N 13/00* (2006.01)

(56) References Cited

U.S. PATENT DOCUMENTS

| | | | | |
|---|---|---|---|---|
| 2011/0130653 | A1* | 6/2011 | Wang | A61B 6/505 |
| | | | | 600/425 |
| 2012/0172700 | A1* | 7/2012 | Krishnan | A61B 6/032 |
| | | | | 600/407 |
| 2013/0060146 | A1* | 3/2013 | Yang | A61B 90/30 |
| | | | | 600/476 |
| 2013/0287276 | A1* | 10/2013 | Weiss | B60R 25/00 |
| | | | | 382/131 |

OTHER PUBLICATIONS

William M. Wells III et al., "Multi-modal volume registration by maximization of mutual information," Medical Image Analysis, 1996, pp. 35-51, vol. 1, No. 1.
Communication dated Nov. 22, 2016 from the Japanese Patent Office in corresponding Application No. 2014-192152.
Communication dated Jun. 2, 2016, from the German Patent Office in counterpart German application No. 10 2015 114 513.8.

* cited by examiner

MEDICAL IMAGE PROCESSING APPARATUS, METHOD, AND RECORDING MEDIUM

CROSS-REFERENCE TO RELATED APPLICATIONS

The present application claims priority under 35 U.S.C. §119 to Japanese Patent Application No. 2014-192152 filed on Sep. 22, 2014. The above application is hereby expressly incorporated by reference, in its entirety, into the present application.

BACKGROUND

The present disclosure relates to a medical image processing apparatus, method, and program for recognizing a vertebra included in a medical image.

A spinal cord is a very important region as it plays a role of conveying messages between a brain and each body region. For this reason, the spinal cord is protected by a plurality of vertebrae (a spine). In addition, it is practiced to confirm the presence or absence of damage or a lesion in a vertebra by interpreting a tomographic image obtained by scanning a subject. At this time, it is necessary to identify each vertebra, for example, to report a damaged or lesioned vertebra. Therefore, various image processing algorithms for separating and recognizing a plurality of vertebrae based on a tomographic image obtained by scanning a subject and labeling each vertebra.

For example, Japanese Unexamined Patent Publication No. 2011-131040 proposes a method for generating, with a three-dimensional image obtained from tomographic images of a computed tomography (CT) image, a magnetic resonance imaging (MRI) image, or the like as the target, tomographic images of planes intersecting and parallel to the central axis of each vertebra, calculating a characteristic amount representing sharpness of a cross-sectional shape in each tomographic image and a characteristic amount representing regularity of an array of vertebrae, identifying an area of each vertebra by identifying a position of an intervertebral disc located between each vertebra based on these characteristic amounts, and further labeling the identified area of each vertebra.

The literature M. Lootus et al., "Vertebrae Detection and Labelling in Lumbar MR Images", MICCAI Workshop: Computational Methods and Clinical Applications for Spine Imaging, 2013 proposes a method of extrapolating vertebrae and a sacrum using Deformable Part Model and Dynamic Programming. The method described in the aforementioned literature allows extrapolation of a sacrum and labeling of vertebrae with reference to the sacrum.

SUMMARY

In a case where the target image includes only a portion of a spine, for example, only the thoracic spine, however, the positions of the vertebrae cannot be recognized by the use of the method described in Japanese Unexamined Patent Publication No. 2011-131040 or in M. Lootus et al., "Vertebrae Detection and Labelling in Lumbar MR Images", MICCAI Workshop: Computational Methods and Clinical Applications for Spine Imaging, 2013, and as a result the vertebrae cannot be labeled.

The present disclosure has been developed in view of the circumstances described above. The present disclosure allows, even for an image that includes only a portion of a vertebra, labeling the vertebra included in the image, in a medical image processing apparatus, method, and program.

A medical image processing apparatus of the present disclosure includes:

a determination means that makes a determination as to whether or not at least either one of at least a portion of an upper end vertebra and at least a portion of a lower end vertebra is included in a first medical image of a subject;

an image obtaining means that obtains, if the determination is negative, a second medical image that allows recognition of a label of the vertebra of the subject; and a labeling means that aligns the first medical image with the second medical image and labels the vertebra included in the first medical image.

The term "at least a portion of an upper end vertebra" refers to a portion of a plurality of vertebrae constituting a spine that can be recognized as the upper end vertebra. Therefore, it may be the entire upper end vertebra or a portion thereof.

The term "at least a portion of a lower end vertebra" refers to a portion of a plurality of vertebrae constituting a spine that can be recognized as the lower end vertebra. Therefore, it may be the entire lower end vertebra or a portion thereof.

The "label" may be any information as long as it allows recognition of the anatomical position of the vertebra. For example, the label may be an anatomical symbol, a number, and a combination of a symbol and a number specific to each vertebra. In addition, the label may be a symbol, a number, a combination of a symbol and a number, and the like with reference to a specific vertebra.

In the medical image processing apparatus according to the present disclosure, the labeling means may be a means that labels, when the determination is positive, the vertebra included in the first medical image based on either one of information of at least a portion of the upper end vertebra and at least a portion of the lower end vertebra included in the first medical image.

Further, in the medical image processing apparatus according to the present disclosure, the image obtaining means may be a means that obtains a medical image that includes at least either one of at least a portion of the upper end vertebra and at least a portion of the lower end vertebra of the subject as the second medical image.

Still further, in the medical image processing apparatus according to the present disclosure, the image obtaining means may be a means that obtains an image in which a label of at least one vertebra of the subject is known as the second medical image.

Further, in the medical image processing apparatus according to the present disclosure, the upper end vertebra may be at least either one of a first cervical vertebra and a second cervical vertebra.

Still further, in the medical image processing apparatus according to the present disclosure, the lower end vertebra may be at least either one of a fifth lumbar vertebra and a sacrum.

Further, in the medical image processing apparatus according to the present disclosure, the image obtaining means may be a means that obtains, if a plurality of medical images that allow recognition of a label of the vertebra of the subject is present, a medical image captured by the same imaging method as that of the first medical image as the second medical image.

Still further, in the medical image processing apparatus according to the present disclosure, the image obtaining means may be a means that obtains, if a plurality of medical images that allow recognition of a label of the vertebra of the subject is present, a medical image which is close in imaging time to the first medical image as the second medical image.

As for the "medical image which is close in imaging time", a medical image which is closest in imaging time is preferably used, but not limited to this and a medical image captured within a predetermined number of days from the imaging time of the first medical image may be used.

A medical image processing method according to the present disclosure includes the steps of:

making a determination as to whether or not at least either one of at least a portion of an upper end vertebra and at least a portion of a lower end vertebra is included in a first medical image of a subject;

obtaining, if the determination is negative, a second medical image that allows recognition of a label of the vertebra of the subject; and aligning the first medical image with the second medical image and labeling the vertebra included in the first medical image.

Note that medical image processing method according to the present disclosure may be provided as a program to be executed by a computer.

For labeling vertebrae, it is necessary to use at least either one of the upper end vertebra and the lower end vertebra as the reference. According to the present disclosure, a determination is made as to whether or not at least either one of at least a portion of an upper end vertebra and at least a portion of a lower end vertebra is included in a first medical image of a subject. Then, if the determination is negative, a second medical image that allows recognition of a label of the vertebra of the subject is obtained, the first and the second medical images are aligned, and the vertebra included in the first medical image is labeled using the second medical image. Therefore, even in a case where the first medical image includes only a portion of a vertebra, the vertebra included in the first medical image can be labeled using the second medical image.

DETAILED DESCRIPTION OF THE PREFERRED EMBODIMENTS

Figure 1:
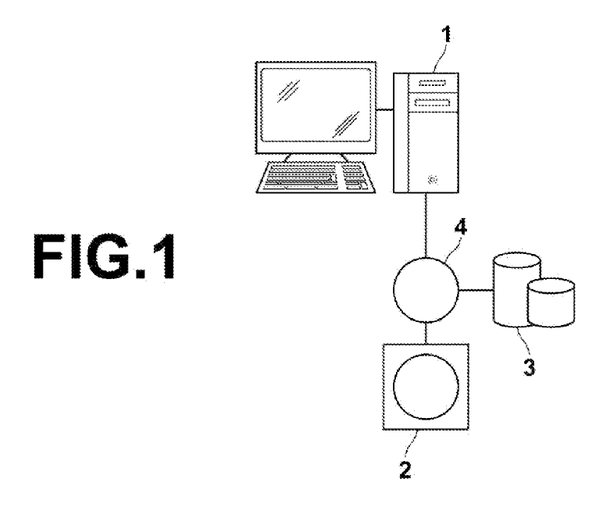
FIG. 1 is a hardware configuration diagram of a diagnosis support system to which a medical image processing apparatus according to an embodiment of the present disclosure is applied, illustrating an overview thereof.

Hereinafter, embodiments of the present disclosure will be described with reference to the accompanying drawings. FIG. 1 is a hardware configuration of a diagnosis support system to which a medical image processing apparatus according to an embodiment of the present disclosure is applied, illustrating an overview thereof. As illustrated in FIG. 1, the system includes a medical image processing apparatus 1 according to the present embodiment, a three-dimensional image capturing apparatus 2, and an image storage server 3 which are communicatively connected through a network 4.

The three-dimensional image capturing apparatus 2 is an apparatus that captures a diagnostic target region of a subject and generates a three-dimensional image representing the region. More specifically, the apparatus 2 is CT equipment, MRI equipment, positron emission tomography (PET) equipment, or the like. The three-dimensional image generated by the three-dimensional image capturing apparatus 2 is transmitted to the image storage server 3 and stored therein. It is assumed in the present embodiment that the diagnostic target region of the subject is a vertebra, the three-dimensional image capturing apparatus 2 is MRI equipment, and the three-dimensional image is a MRI image.

The image storage server 3 is a computer that stores and manages various types of data, and includes a large capacity external storage device and database management software. The image storage server 3 communicates with the other apparatuses via the wire or wireless network 4 to send and receive image data and the like. More specifically, the image storage server 3 obtains image data of a three-dimensional image generated by the three-dimensional image capturing apparatus 2 and similar data via the network and manages them by storing in a storage medium, such as the large capacity external storage device. The image data storage format and communication between each equipment are based on a protocol such as the digital imaging and communication in medicine (DICOM). Further, a DICOM standard tag is attached to the three-dimensional image. The tag includes various types of information, including a patient name, information representing the imaging apparatus, date and time of imaging, imaged region, and the like.

The medical image processing apparatus 1 is one computer on which a medical image processing program of the present disclosure is installed. The computer may be a workstation or a personal computer directly operated by the doctor who performs diagnosis, or a server computer connected thereto via the network. The medical image processing program is distributed by being recorded on a recording medium, such as DVD, CD-ROM, or the like, and installed on the computer from the recording medium. Otherwise, the program is stored in a storage device of the server computer connected to the network or in a network storage in an accessible state from the outside, and downloaded and installed on the computer used by the doctor upon request.

Figure 2:
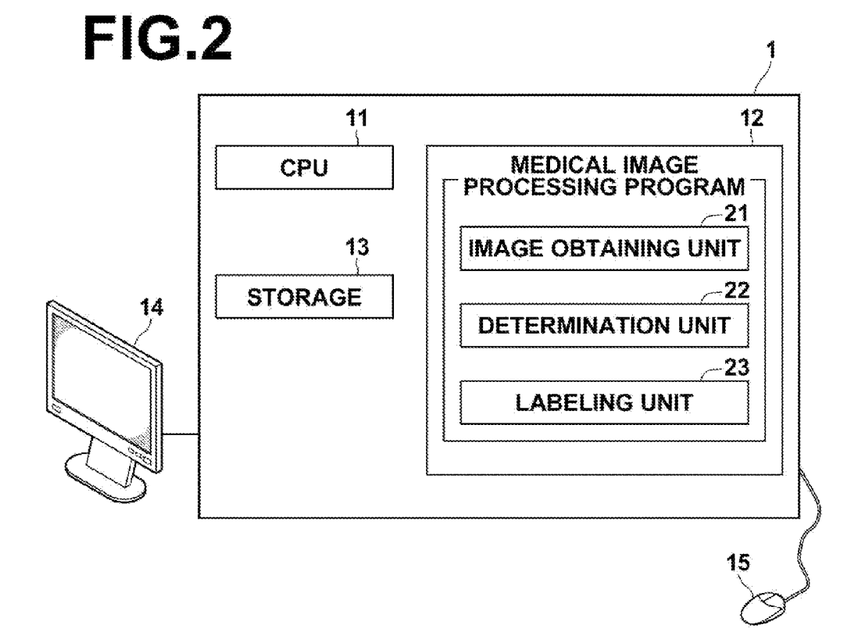
FIG. 2 shows a medical image processing apparatus realized by installing a medical image processing program on a computer, illustrating a schematic configuration thereof.

FIG. 2 shows a medical image processing apparatus realized by installing the medical image processing program on a computer, illustrating a schematic configuration thereof. As illustrated in FIG. 2, the medical image processing apparatus 1 includes a CPU 11, a memory 12, and a storage 13 as a configuration of a standard workstation. In addition, a display 14 and an input device 15, such as a mouse, are connected to the medical image processing apparatus 1.

The storage 13 includes various types of information, including a three-dimensional image obtained from the image storage server 3 via the network 4 and an image generated through the processing performed in the medical image processing apparatus 1.

The memory 12 stores the medical image processing program. The medical image processing program defines, as the processes executed by the CPU 11, a first image obtaining process for obtaining a first three-dimensional image V1 which includes a diagnostic target vertebra of a subject, a determination process for determining whether or not the first three-dimensional image V1 includes at least either one of at least a portion of an upper end vertebra and at least a portion of a lower end vertebra, a second image obtaining process for obtaining, if the determination is negative, a second three-dimensional image V2 that allows recognition of a label of a vertebra of the subject, and a labeling process for aligning the first three-dimensional image V1 with the second three-dimensional image V2 and labeling the vertebra included in the first three-dimensional image V1.

Execution of these processes by the CPU 11 according to the program causes the computer to function as an image obtaining unit 21, a determination unit 22, and a labeling unit 23. The medical image processing apparatus 1 may include a plurality of CPUs for performing the first and the second image obtaining processes, the determination process, and the labeling process respectively.

The image obtaining unit 21 obtains the first and the second three-dimensional images V1, V2 from the image storage server 3. In a case where the three-dimensional images V1, V2 have already been stored in the storage 13, the image obtaining unit 21 may obtain the images from the storage 13.

Figure 3:
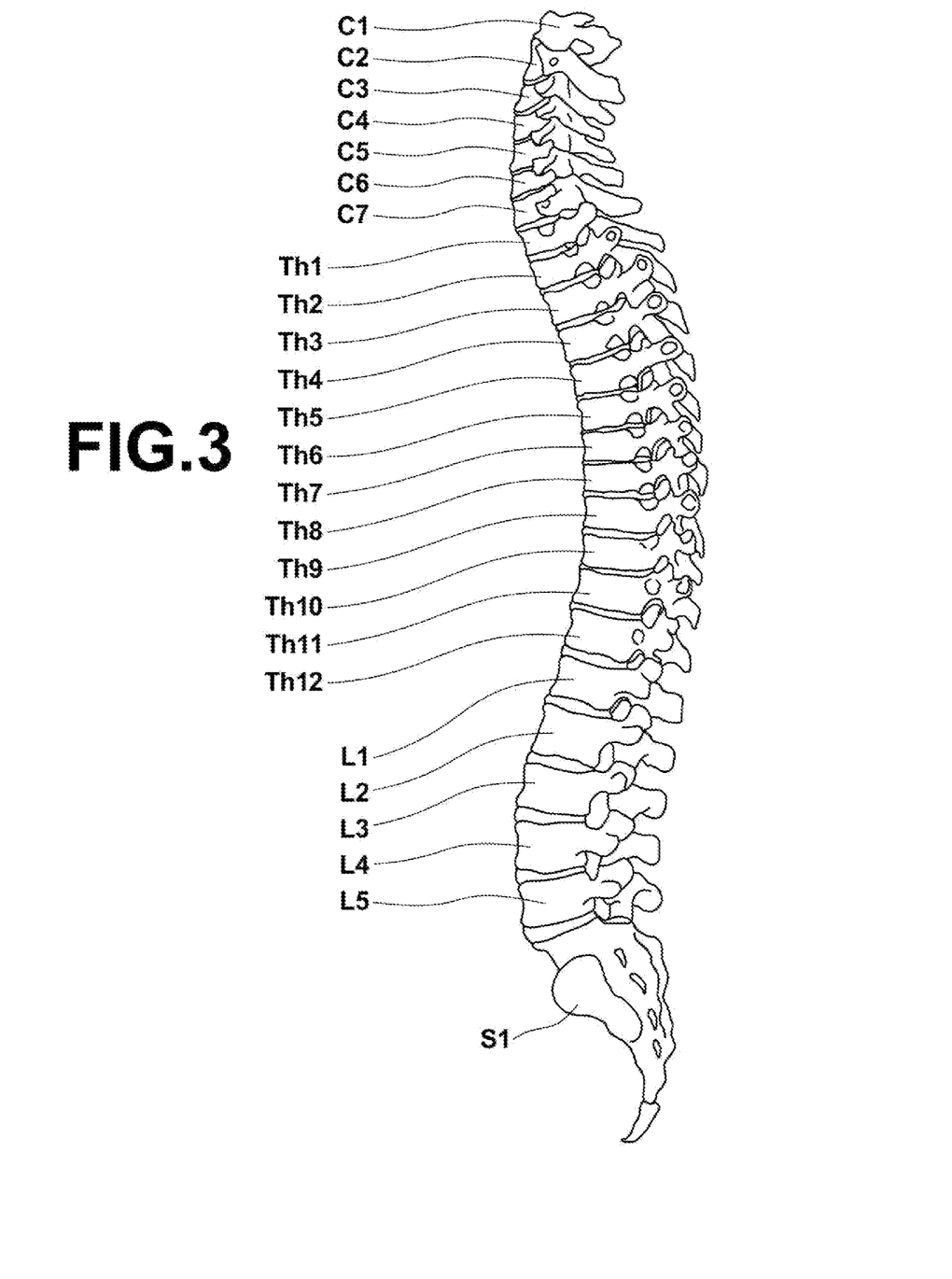
FIG. 3 schematically illustrates a sagittal image representing an array of vertebrae.

The determination unit 22 determines whether or not the first three-dimensional image V1 includes at least either one of at least a portion of an upper end vertebra and at least a portion of a lower end vertebra, and outputs a result of the determination to the image obtaining unit 21 and labeling unit 23. FIG. 3 schematically illustrates a sagittal image representing an array of vertebrae. As shown in FIG. 3, each vertebra is anatomically labeled. Here, the spine is composed of four portions of cervical spine, thoracic spine, lumbar spine, and sacrum. The cervical spine is composed of seven vertebrae and anatomically labeled as C1 to C7. The thoracic spine is composed of twelve vertebrae and anatomically labeled as Th1 to Th12. The lumbar spine is composed of five vertebrae and anatomically labeled as L1 to L5. The sacrum is composed of only one bone and anatomically labeled as S1. The present embodiment uses these anatomical labels as the labels to be applied to the vertebrae.

As illustrated in FIG. 3, although vertebrae have a cylindrical shape, the first cervical vertebra and the second cervical vertebra located in an upper end portion, and the fifth lumbar vertebra and the sacrum located in a lower end portion have characteristic shapes different from those of the other vertebrae. For this reason, the determination unit 22 of the present embodiment uses, as the target for making a determination, at least either one of the first cervical vertebra and the second cervical vertebra as the upper end vertebra, and at least either one of the fifth lumbar vertebra and the sacrum as the lower end vertebra.

Note that the determination unit 22 performs at least either one of a first determination which is a determination as to whether or not the first three-dimensional image V1 includes at least a portion of the upper end vertebra, i.e., at least an area in which the upper end vertebra can be recognized and a second determination which is a determination as to whether or not the first three-dimensional image V1 includes at least a portion of the lower end vertebra, i.e., at least an area in which the lower end vertebra can be recognized. In the present embodiment, only the first or the second determination may be made, or both the first and the second determinations may be made. Further, the first determination may be made first and if the first determination is negative, the second determination may be made, while if the first determination is positive, the second determination may not be made. Contrary to this, the second determination may be made first and if the second determination is negative, the first determination may be made, while if the second determination is positive, the first determination may not be made. In this case, if both the first and second determinations are negative, the determination as to whether or not the first three-dimensional image V1 includes at least either one of at least a portion of the upper end vertebra and at least a portion of the lower end vertebra is negative, and otherwise it is positive.

Here, the determination unit 22 is provided with a template having a pattern representing a three-dimensional shape of at least one of the first and the second cervical vertebrae for the first determination. Further, the determination unit 22 is provided with a template having a pattern representing a three-dimensional shape of at least one of the fifth lumbar vertebra and the sacrum for the second determination. The determination unit 22 performs matching between the first three-dimensional image and the template to search for an area having a shape which is the same as that of the pattern of the template. Then, if the area is found, the first and the second determinations are positive.

Figure 4:
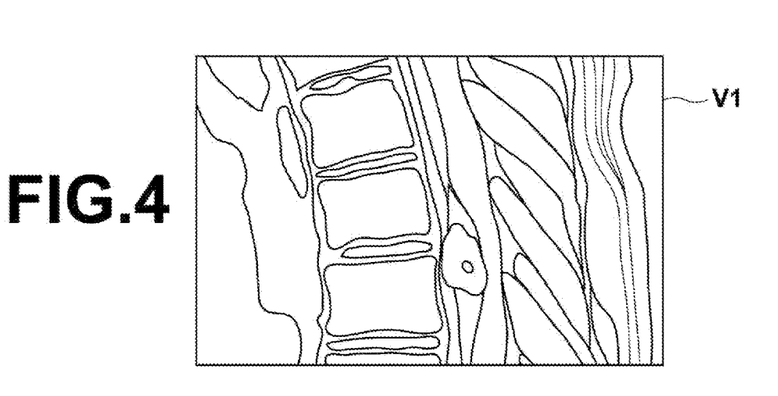
FIG. 4 shows an example of a first three-dimensional image.
Figure 5:
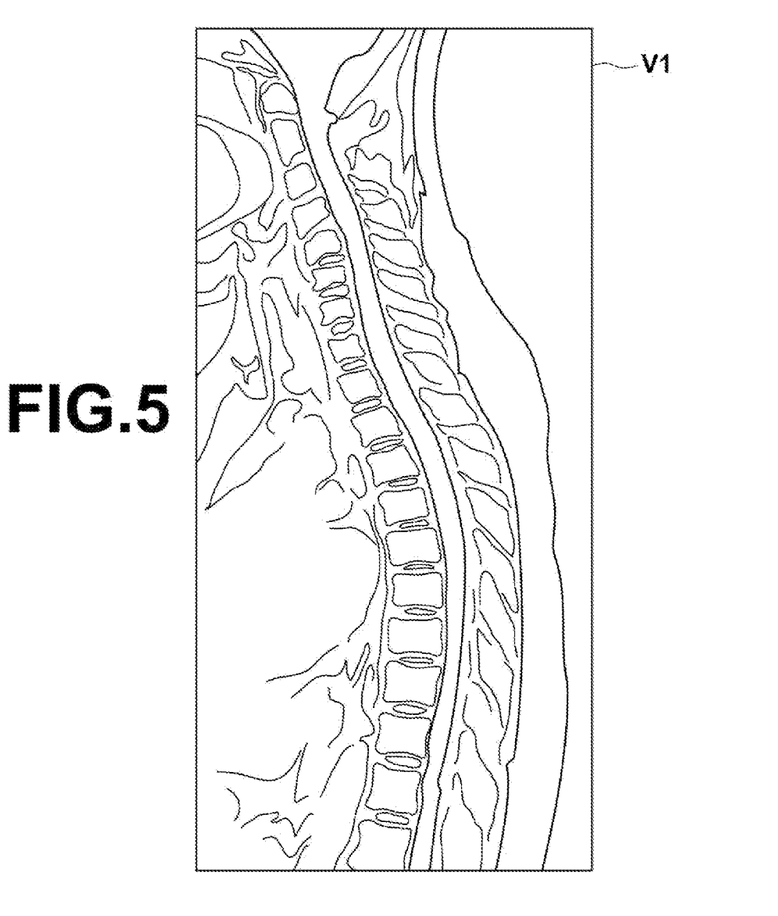
FIG. 5 shows an example of a second three-dimensional image.
Figure 6:
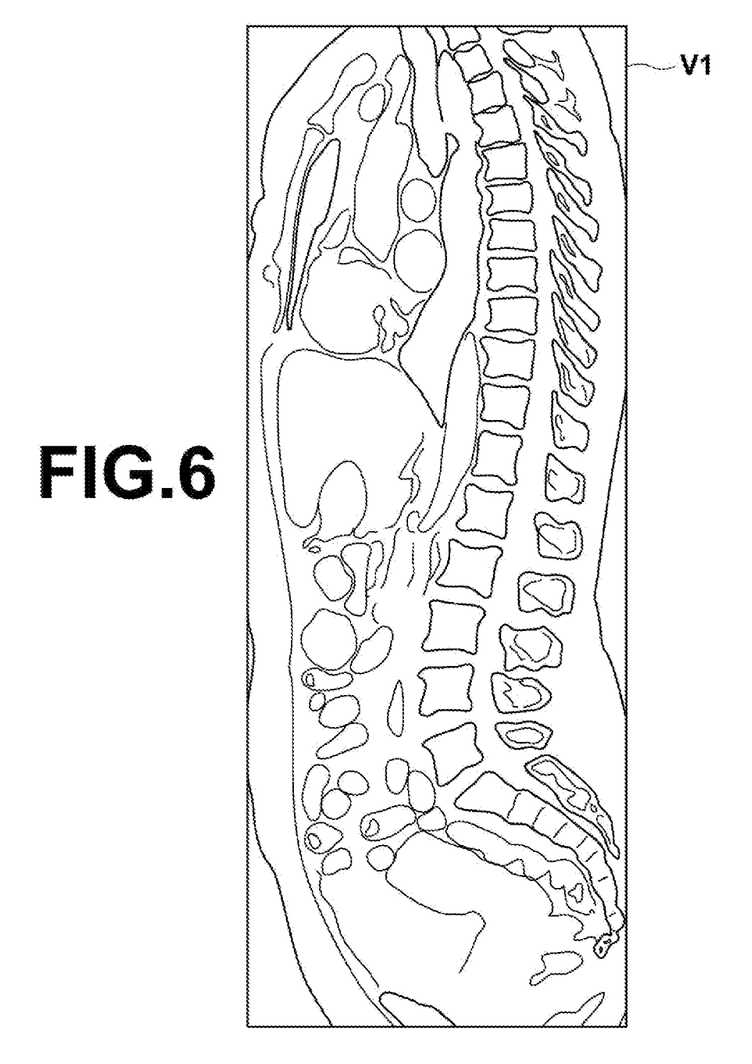
FIG. 6 shows another example of a second three-dimensional image.

Here, if the first three-dimensional image V1 includes only a portion of the thoracic spine as shown in FIG. 4, the determination made by the determination unit 22 is negative. On the other hand, if the first three-dimensional image V1 includes at least either one of the first and the second cervical vertebrae as shown in FIG. 5, or if the first three-dimensional image V1 includes at least either one of the fifth lumbar vertebra and the sacrum as shown in FIG. 6, the determination made by the determination unit 22 is positive. Note that in each of FIGS. 4 to 6, a sagittal image passing through the center of vertebrae generated from a three-dimensional image is shown for the purpose of explanation.

The labeling unit 23 performs a first labeling process if a determination made by the determination unit 22 is negative and, if positive, performs a second labeling process. The first labeling process will be described first. If a determination made by the determination unit 22 is negative, the image obtaining unit 21 obtains a second three-dimensional image V2 that allows recognition of a label of a vertebra of the subject of the first three-dimensional image V1 from the image storage server 3.

Here, a DICOM standard tag is attached to a three-dimensional image stored in the image storage server 3. The tag includes a patient name, information representing the imaging apparatus, date and time of imaging, imaged region, and the like. The image obtaining unit 21 obtains a three-dimensional image whose tag includes the same patient name as that of the first three-dimensional image V1 and allows recognition of a label of a vertebra, as a second three-dimensional image V2. As for the three-dimensional image that allows recognition of a label of a vertebra, an image in which vertebrae have already been labeled and information to that effect is included in the tag may be used. Alternatively, an image with a tag that includes information indicating that at least a portion of the upper end vertebra or at least a portion of the lower end vertebra is included in the image may be used.

Here, in a case where a plurality of three-dimensional images of the same patient that allow recognition of a label of a vertebra is stored in the image storage server 3, a three-dimensional image obtained by the same imaging method as that of the first three-dimensional image V1 is obtained as the second three-dimensional image V2. For example, in a case where the first three-dimensional image V1 is a MRI image, a MRI image is obtained as the second three-dimensional image V2. Further, a three-dimensional image closest in imaging time to the first three-dimensional image V1 may be obtained as the second three-dimensional image V2. Still further, a determination may be made as to whether or not a three-dimensional image obtained by the same imaging method as that of the first three-dimensional image V1 is stored in the image storage server 3 and if the determination is negative, a three-dimensional image closest in imaging time to the first three-dimensional image V1 may be obtained as the second three-dimensional image V2.

If the second three-dimensional image V2 is an image whose tag includes labeling information of vertebrae included in the image, the labeling unit 23 labels the vertebra included in the first three-dimensional image V1 using the obtained three-dimensional image V2. On the other hand, if the second three-dimensional image V2 is an image whose tag does not include labeling information of vertebrae included in the image, and the image includes at least a portion of the upper end vertebra and at least a portion of the lower end vertebra, the labeling unit 23 recognizes the position of each vertebra included in the second three-dimensional image V2 and labels each vertebra. The processing of recognizing the position of each vertebra and labeling each vertebra is identical to a second labeling process, to be described later and, therefore, a detailed description is omitted here.

Figure 7:
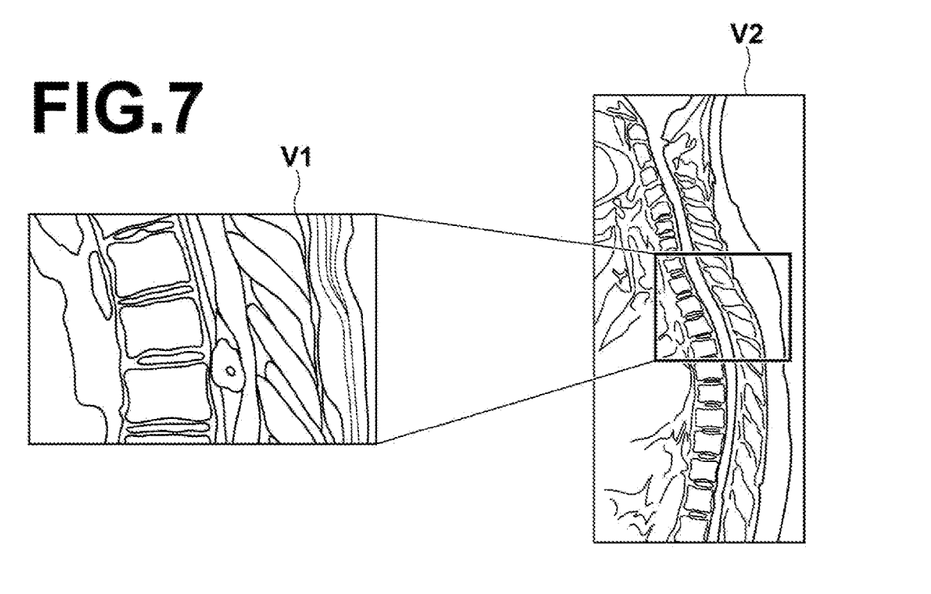
FIG. 7 is a drawing for explaining alignment.

Then, the labeling unit 23 performs alignment between the first three-dimensional image V1 and the second three-dimensional image V2. As an alignment method, matching may be performed between the first three-dimensional image V1 and the second three-dimensional image V2 to search for an area that includes a vertebra having the same shape as that of a vertebra included in the first three-dimensional image V1. In a case where the imaging method is different between the first three-dimensional image V1 and the second three-dimensional image V2, for example, if the first three-dimensional image V1 is a MRI image while the second three-dimensional image V2 is a CT image, the alignment may be performed using the method described in W. M. Wells III, et al., "Multi-modal volume registration by maximization of mutual information", Medical Image Analysis, Vol. 1, No. 1, pp. 35-51, 1996 (Reference Literature 1). This causes the first three-dimensional image V1 and the second three-dimensional image V2 to be aligned, as illustrated in FIG. 7. Here, the labels of the vertebrae are already known in the second three-dimensional image V2. In the second three-dimensional image V2, if the labels of the vertebrae included in the area corresponding to the first three-dimensional image V1 are Th2, Th3, and Th4, the vertebrae included in the first three-dimensional image V1 can be labeled as Th2, Th3, and Th4.

Next, a second labeling process will be described. The second labeling process is processing to label vertebrae included in the first three-dimensional image V1 based on at least either one of information of at least a portion of the upper end vertebra and at least a portion of the lower end vertebra included in the first three-dimensional image V1. The labeling unit 23 performs the second labeling process using, for example, the method described in Japanese Unexamined Patent Publication No. 2011-131040. That is, the labeling unit 23 detects a central axis of each vertebra from the first three-dimensional image V1 and generates tomographic images of planes intersecting and parallel to the detected central axis of each vertebra. Then, the labeling unit 23 recognizes the position of each vertebra based on a characteristic amount representing sharpness of a cross-sectional shape in each tomographic image and a characteristic amount representing regularity of an array of the vertebrae. In a case where the first three-dimensional image V1 includes at least a portion of the upper end vertebra, the labeling unit 23 labels the recognized vertebrae in order from the upper end. Further, in a case where the first three-dimensional image V1 includes at least a portion of the lower end vertebra, the labeling unit 23 labels the recognized vertebrae in order from the lower end.

Note that, in a case where the first three-dimensional image V1 includes a sacrum, the labeling unit 23 may recognize the sacrum using the method described in M. Lootus et al., "Vertebrae Detection and Labelling in Lumbar MR Images", MICCAI Workshop: Computational Methods and Clinical Applications for Spine Imaging, 2013, and may label the vertebrae with reference to the sacrum.

The method of labeling vertebrae is not limited to those described above and any method may be used.

Figure 8:
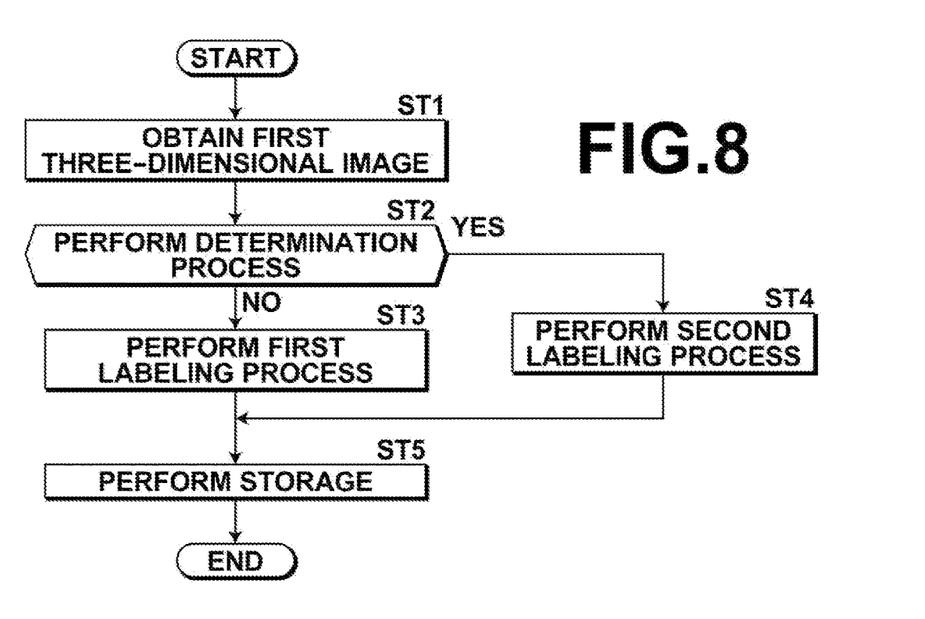
FIG. 8 is a flowchart illustrating processing performed in the present embodiment.

Processing performed in the present embodiment will now be described. FIG. 8 is a flowchart illustrating processing performed in the present embodiment. First, the image obtaining unit 21 obtains a diagnostic target first three-dimensional image V1 from the image storage server 3 (step ST1), and the determination unit 22 performs a determination as to whether or not the first three-dimensional image V1 includes at least a portion of the upper end vertebra, i.e., at least an area in which the upper end vertebra can be recognized (determination process, step ST2). If step ST2 is negative, the labeling unit 23 performs the first labeling process (step ST3). On the other hand, if step ST2 is positive, the labeling unit 23 performs the second labeling process (step ST4). Then the labeling unit 23 stores the first three-dimensional image V1 in which the vertebrae are labeled (step ST5), and the processing is terminated.

In this way, in the present embodiment, if a determination made by the determination unit 22 is negative, a second three-dimensional image V2 is obtained, then the first three-dimensional image V1 and the second three-dimensional image V2 are aligned, and a vertebra included in the first three-dimensional image V1 is labeled using the second three-dimensional image V2. Therefore, even in a case where the first three-dimensional image V1 includes only a portion of a vertebra, the vertebra included in the first three-dimensional image V1 may be labeled.

Further, in a case where a plurality of three-dimensional images usable as the second three-dimensional image V2 is present, a three-dimensional image captured by the same imaging method as that of the first three-dimensional image V1 is obtained as the second three-dimensional image V2. This allows the vertebra included in the first three-dimensional image V1 to be labeled accurately.

Still further, in a case where a plurality of three-dimensional images usable as the second three-dimensional image V2 is present, a three-dimensional image closest in imaging time to the first three-dimensional image V1 is obtained as the second three-dimensional image V2. This allows the vertebra included in the first three-dimensional image V1 to be labeled accurately.

In the foregoing embodiment, when performing the first labeling process, there may be a case where no image that allows recognition of a vertebra label is stored in the image storage server 3. In this case, the labeling unit 23 may display a message that the vertebra cannot be labeled on the display 14, since the vertebra included in the first three-dimensional image cannot be labeled. Instead of or in addition to the message display, a speech message may be outputted.

Further, in the foregoing embodiment, a vertebra is labeled using three-dimensional images as the first and the second medical image of the present disclosure, but the labeling of a vertebra may be performed with a two-dimensional X-ray image obtained by X-ray imaging or a tomographic image of a sagittal cross-section passing through the center of the vertebrae as the target. In this case, different types of images may be used between the first and the second medical images, like the first medical image is a three-dimensional image while the second medical image is an X-ray image. Further, in this case, a pseudo two-dimensional X-ray image may be generated by projecting the three-dimensional image of the first medical image and labeling of a vertebra may be performed with the pseudo X-ray image as the target.

What is claimed is:

1. A medical image processing apparatus, comprising:
   a memory configured to store instructions; and
   a processor configured to execute the stored instructions, which when executed by the processor cause the processor to:
   determine whether: a) at least a portion of an upper end vertebra, b) at least a portion of a lower end vertebra, and c) both of said at least the portion of the upper end vertebra and said at least the portion of the lower vertebra, is included in a first medical image of a subject;
   obtain, if the determination is negative, a second medical image that allows recognition of a label of the vertebra of the subject; and
   align the first medical image with the second medical image and label the vertebra included in the first medical image,
   wherein, if a plurality of medical images that allow recognition of a label of the vertebra of the subject is present, the processor is further configured to obtain a medical image which is close in imaging time to the first medical image as the second medical image.

2. The medical image processing apparatus of claim 1, wherein, when the determination is positive, the processor is further configured to label the vertebra included in the first medical image based on either one of information of at least a portion of the upper end vertebra and at least a portion of the lower end vertebra included in the first medical image.

3. The medical image processing apparatus of claim 1, wherein the processor is further configured to obtain a medical image that includes at least either one of at least a portion of the upper end vertebra and at least a portion of the lower end vertebra of the subject as the second medical image.

4. The medical image processing apparatus of claim 1, wherein the processor is further configured to obtain an image in which a label of at least one vertebra of the subject is known as the second medical image.

5. The medical image processing apparatus of claim 1, wherein the upper end vertebra is at least either one of a first cervical vertebra and a second cervical vertebra.

6. The medical image processing apparatus of claim 1, wherein the lower end vertebra is at least either one of a fifth lumbar vertebra and a sacrum.

7. The medical image processing apparatus of claim 1, wherein, if a plurality of medical images that allow recognition of a label of the vertebra of the subject is present, the processor is further configured to obtain a medical image captured by the same imaging method as that of the first medical image as the second medical image.

8. A medical image processing method, comprising:
   determining, by a processor, whether: a) at least a portion of an upper end vertebra, b) at least a portion of a lower end vertebra, and c) both of said at least portion of the upper end vertebra and said at least the portion of the lower end vertebra, is included in a first medical image of a subject;
   in response to the determining being negative, obtaining a second medical image that allows recognition of a label of the vertebra of the subject;
   aligning, by the processor, the first medical image with the second medical image and labeling the vertebra included in the first medical image; and
   output results of the labeling,
   wherein, if a plurality of medical images that allow recognition of a label of the vertebra of the subject is present, obtaining a medical image which is close in imaging time to the first medical image as the second medical image.

9. The method of claim 8, wherein the outputting the results comprises displaying, on a display, the labeled first medical image.

10. A non-transitory recording medium containing a medical image processing program for causing a computer to perform:
    determining whether a) at least a portion of an upper end vertebra, b) at least a portion of a lower end vertebra, and c) both of said at least portion of the upper end vertebra and said at least the portion of the lower end vertebra, is included in a first medical image of a subject;
    obtaining, if the determining is negative, a second medical image that allows recognition of a label of the vertebra of the subject;
    aligning the first medical image with the second medical image and labeling the vertebra included in the first medical image; and
    outputting results of the labeling,
    wherein, if a plurality of medical images that allow recognition of a label of the vertebra of the subject is present, obtaining a medical image which is close in imaging time to the first medical image as the second medical image.

11. The non-transitory computer readable medium of claim 10, wherein the outputting the results of the labeling comprises displaying on a display the labeled first medical image.

* * * * *